US007849861B2

(12) United States Patent
Ravikumar

(10) Patent No.: US 7,849,861 B2
(45) Date of Patent: Dec. 14, 2010

(54) INTRAVASCULAR CATHETER DEVICE FOR SELECTIVE OCCLUSION OF ILIAC VASCULATURE

(76) Inventor: Sundaram Ravikumar, 265 Hardscrabble Rd., Briarcliff Manor, NY (US) 10510

( * ) Notice: Subject to any disclaimer, the term of this patent is extended or adjusted under 35 U.S.C. 154(b) by 75 days.

(21) Appl. No.: 12/113,220

(22) Filed: May 1, 2008

(65) Prior Publication Data
US 2009/0275889 A1 Nov. 5, 2009

(51) Int. Cl.
A61B 19/00 (2006.01)
(52) U.S. Cl. .................. 128/898; 604/907; 604/101.05
(58) Field of Classification Search ............ 604/101.05; 600/36
See application file for complete search history.

(56) References Cited

U.S. PATENT DOCUMENTS

| 4,404,971 | A | 9/1983 | Le Veen et al. |
| 4,708,140 | A | 11/1987 | Baron |
| 5,312,344 | A | 5/1994 | Grinfield et al. |
| 5,320,605 | A | 6/1994 | Sahota |
| 5,458,574 | A | 10/1995 | Machold et al. |
| 5,505,701 | A | 4/1996 | Anaya Fernandez de Lomana |
| 5,810,757 | A | 9/1998 | Sweezer, Jr. et al. |
| 5,820,593 | A | 10/1998 | Safar et al. |
| 6,148,222 | A | 11/2000 | Ramsey, III |
| 6,148,825 | A | 11/2000 | Anderson et al. |
| 6,165,196 | A | 12/2000 | Stack et al. |
| 6,565,552 | B1 | 5/2003 | Barbut |
| 6,585,689 | B1 | 7/2003 | Macoviak et al. |
| 6,719,724 | B1 | 4/2004 | Walker et al. |
| 7,335,192 | B2 | 2/2008 | Keren et al. |
| 2001/0001806 | A1* | 5/2001 | Turnlund et al. ............... 600/3 |

2007/0135793 A1 6/2007 Barbut et al.

FOREIGN PATENT DOCUMENTS

WO WO 01/19442 3/2001

OTHER PUBLICATIONS

Gill et al. "A New Triple-Balloon, Four-Channel Vascular Catheter for Use in Renal Transplantation." May 1994. The Journal of Urology: vol. 151, 1416-1419.*

(Continued)

Primary Examiner—Nicholas D Lucchesi
Assistant Examiner—Leah Stohr
(74) Attorney, Agent, or Firm—Gordon & Jacobson, PC

(57) ABSTRACT

An improved catheter device for selectively isolating and occluding a portion of the iliac vasculature of a patient includes an elongate hollow catheter shaft which is advanceable though the vascular system of the patient. The catheter shaft has a proximal portion that extends out from the patient and a distal portion adapted to be disposed within the iliac vasculature of the patient. A plurality of expandable members are disposed on the distal portion. One expandable member is dimensioned and configured so that when expanded it rests within the bifurcation of the descending aorta to the common iliac arteries (and/or within the bifurcation of the inferior vena cava that leads to the common iliac veins) so as to fixate the catheter within the iliac vasculature of the patient. At least two other expandable members are spaced apart from the fixation member and configured to selectively isolate and occlude blood flow through different portions of the iliac vasculature.

11 Claims, 7 Drawing Sheets

OTHER PUBLICATIONS

Gill, et al. A New Triple Balloon, Four-Channel Vascular Catheter For Use In Renal Transplantation. The Journal of Urology. vol. 151, 1416-1419. May 1994.*

"Stent-Graft for Repair of Abdominal Aortic Aneurysm"; Grand Rounds; Interventional Radiology; Society of Cardiovascular & Interventional Radiology: 1999.

"Intra-aortic Balloon Pump"; Cardiology in Critical Care; IABP; Apr. 30, 2004.

"Remote Access Perfusion"; Superior Cannulation for Reducing Trauma; Estec, Oct. 21, 2004.

"Use of the intra-aortic balloon pump to stop gastrointestinal bleeding"; by CD Karkos, IA Bruce, and ME Lambert; Sep. 2001.

* cited by examiner

INTRAVASCULAR CATHETER DEVICE FOR SELECTIVE OCCLUSION OF ILIAC VASCULATURE

BACKGROUND OF THE INVENTION

1. Field of the Invention

This invention relates broadly to intravascular catheter devices and associated methods for vascular applications. More particularly, this invention relates to intravascular catheter device for vasculature occlusion and associated methods.

2. State of the Art

Kidney transplantation is the organ transplant of a kidney in a patient with end-stage renal disease. Kidney transplantation is typically classified as deceased-donor (formerly known as cadaveric) or living-donor transplantation depending on the source of the recipient organ. In most cases, the existing kidneys are not removed because this has been shown to increase the rates of surgical morbidities, and the donor kidney is placed inferior of the normal anatomical location (often in the iliac fossa). As a result, it is often necessary to use a different blood supply for the donor kidney. Typically, the renal artery of the donor kidney, previously branching from the abdominal aorta in the donor, is connected by an anastomosis to the external iliac artery in the recipient, and the renal vein of the donor kidney, previously draining to the inferior vena cava in the donor, is connected by an anastomosis to the external iliac vein in the recipient. Most conventional techniques for vascular anastomosis require the interruption of blood flow through the receiving vessel while the anastomosis is performed. Such interruption of blood flow is typically accomplished by clamping the receiving vessel. In the event that calcium plaque has built up at the clamping location, the clamping can cause the receiving vessel to bleed at the clamp site. Such bleeding is very difficult to repair. Moreover, the clamping can dislodge plaque and it can be carried to the foot or brain as an embolism. In the foot, the embolism can cause gangrene. In the brain, the embolism can cause a stroke.

SUMMARY OF THE INVENTION

It is therefore an object of the invention to provide a minimally invasive surgical device (and corresponding method of treatment) that enables selective isolation and occlusion of blood flow through the iliac vasculature suitable for preparing a portion of the iliac vascular for an anastomosis as part of a kidney transplantation.

It is another object of the invention to provide such a minimally invasive surgical device (and corresponding method of treatment) that employs a catheter device introduced percutaneously through the femoral vasculature.

It is a further object of the invention to provide a surgical device (and corresponding method of treatment) that selectively isolates and occludes a portion of one branch of the iliac vasculature while maintaining blood flow through the other branch of the iliac vasculature and through the abdominal vasculature to the heart.

It is also an object of the invention to provide such a minimally invasive surgical device (and corresponding method of treatment) that is quickly and effectively located (e.g., secured in place) in the iliac vasculature of the patient.

In accord with these objects, which will be discussed in detail below, an improved catheter device for selectively isolating and occluding a portion of the iliac vasculature of a patient includes an elongate hollow catheter shaft which is advanceable though the vascular system of the patient. The catheter shaft has a proximal portion that extends out from the patient and a distal portion adapted to be disposed within the iliac vasculature of the patient. A plurality of expandable members are disposed on the distal portion. One expandable member (referred to herein as the "fixation member" or "fixation balloon") is dimensioned and configured so that when expanded it rests within the bifurcation of the descending aorta to the common iliac arteries (and/or within the bifurcation of the inferior vena cava that leads to the common iliac veins) so as to fixate the catheter within the iliac vasculature of the patient. At least two other expandable members are spaced apart from the fixation member and configured to selectively isolate and occlude blood flow through different portions of the iliac vasculature.

The improved catheter device of the present invention can be quickly fixated within the iliac vasculature and manipulated in order to efficiently isolate and occlude a portion of the iliac vasculature (preferably a portion of the common iliac artery or common iliac vein of the patient). Such isolation and occlusion is suitable for preparing the isolated iliac vascular portion for an anastomosis as part of a kidney transplantation procedure.

According to a preferred embodiment of the invention, the expandable members are realized by inflatable balloons controlled by fluidic pressure supplied thereto via corresponding inflation lumens in the elongate catheter shaft. The balloons are independently inflatable by supply of fluidic pressure thereto. In the preferred embodiment, there are two balloons positioned proximally relative to the seating balloon and spaced apart from one another by a length in the range between 2 cm and 3 cm. One of these balloons has a length in its inflated state in the range between 2 cm and 3.5 cm such that it extends over the bifurcation point of the common iliac artery (or vein) to the external and internal arteries (or veins). Moreover, these two balloons preferably have a maximum radial dimension in the range between 1 cm and 1.5 cm, which ensures that the balloons sealably contact the vessel wall of the iliac vasculature in their inflated state. The catheter shaft has an external diameter in a range between 6 and 8 french with a total length of at least 50 cm.

Additional objects and advantages of the invention will become apparent to those skilled in the art upon reference to the detailed description taken in conjunction with the provided figures.

BRIEF DESCRIPTION OF THE DRAWINGS

FIG. 3E illustrates an anastomosis from the isolated portion of the iliac vasculature to a donor kidney as part of a kidney transplantaton procedure in accordance with the present invention.

DETAILED DESCRIPTION OF THE PREFERRED EMBODIMENTS

The descriptive terms "downstream" and "upstream", when used herein in relation to the patient's vasculature, relate to the direction of normal blood flow and to the direction opposite normal blood flow, respectively, i.e., "upstream" is closer to the heart in the arterial system and further away from the heart in the venous system.

In addition, the terms "proximal" and "distal", when used in relation to instruments used in a surgical procedure refer to directions closer and farther away, respectively, from that end of the instrument which is held or manipulated by the operator performing the procedure.

In addition, the respective "maximum radial dimension" of the expandable members of the catheter device of the present invention extends in a direction substantially orthogonal to the central axis of shaft of the catheter device as described herein.

Figures 1A, 1B:
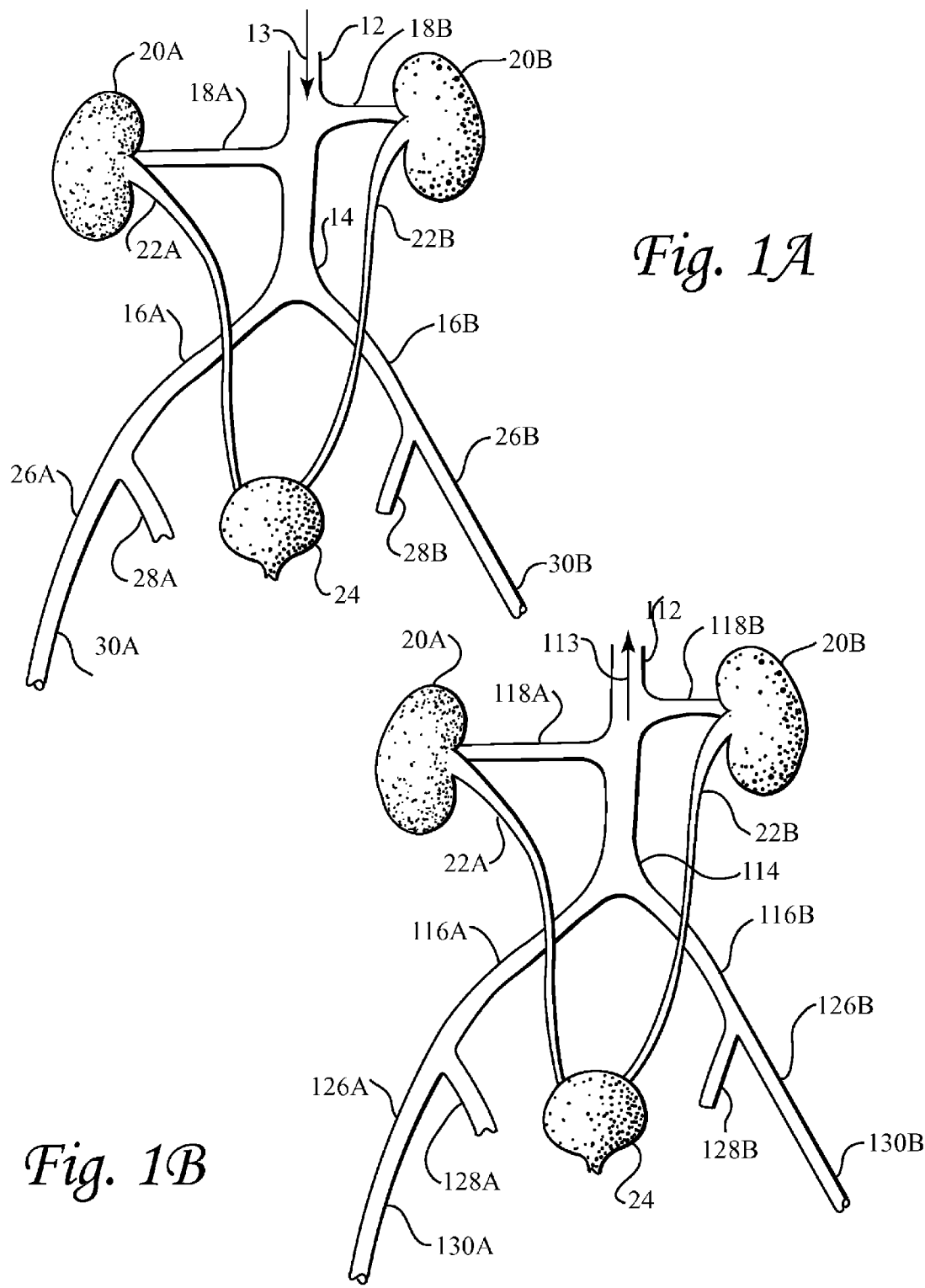
FIGS. 1A and 1B are schematic illustrations of the arterial system and venous system of the abdomen of the human body, respectively.

The arterial system of the abdomen is shown in FIG. 1A. During systole, oxygenated blood leaves the heart and enters the aorta where it flows through the ascending aorta and aortic arch (not shown) and down the descending aorta 12 as depicted by arrow 13. The descending aorta 12 continues to the iliac bifurcation 14, which is a branch that splits into the two common iliac arteries 16A and 16B. The descending aorta 12 gives off numerous branches that supply oxygenated blood to the chest cage and the organs within the chest. These branches include the renal arteries 18A, 18B that supply blood to the kidneys 20A, 20B. Ureters 22A, 22B connect the kidneys 20A, 20B to the bladder 24.

The iliac arterial vasculature includes two branches continuing from the iliac bifurcation 14. The left branch includes the left common iliac artery 16A, which bifurcates into the left external iliac artery 26A and the left internal iliac artery 28A. When the left external iliac artery 26A passes posterior to the inguinal ligament, it becomes the left femoral artery 30A of the left leg. The right branch of the iliac arterial vasculature includes the right common iliac artery 16B, which bifurcates into the right external iliac artery 26B and the right internal iliac artery 28B. When the right external iliac artery 26B passes posterior to the inguinal ligament, it becomes the right femoral artery 30B of the right leg.

The venous system of the abdomen is shown in FIG. 1B. The inferior vena cava 112 carries de-oxygenated blood from the lower half of the body to the right atrium of the heart during diastole. The inferior vena cava 112 extends downward in the abdominal cavity to a bifurcation point 114 joining the left common iliac vein 116A and the right common iliac vein 116B. The inferior vena cava 112 has numerous branches that return de-oxygenated blood from the chest cage and the organs within the chest. These branches include the renal veins 118A, 118B that return blood from the kidneys 20A, 20B.

The iliac venous vasculature includes two branches continuing from this bifurcation point 114. The left branch includes the left common iliac vein 116A, which bifurcates into the left external iliac vein 126A and the left internal iliac vein 128A. When the left external iliac vein 126A passes posterior to the inguinal ligament, it becomes the left femoral vein 130A of the left leg. The right branch of the iliac venous vasculature includes the right common iliac vein 116B, which bifurcates into the right external iliac vein 126B and the right internal iliac vein 128B. When the right external iliac vein 126B passes posterior to the inguinal ligament, it becomes the right femoral vein 130B of the right leg.

Figure 2A:
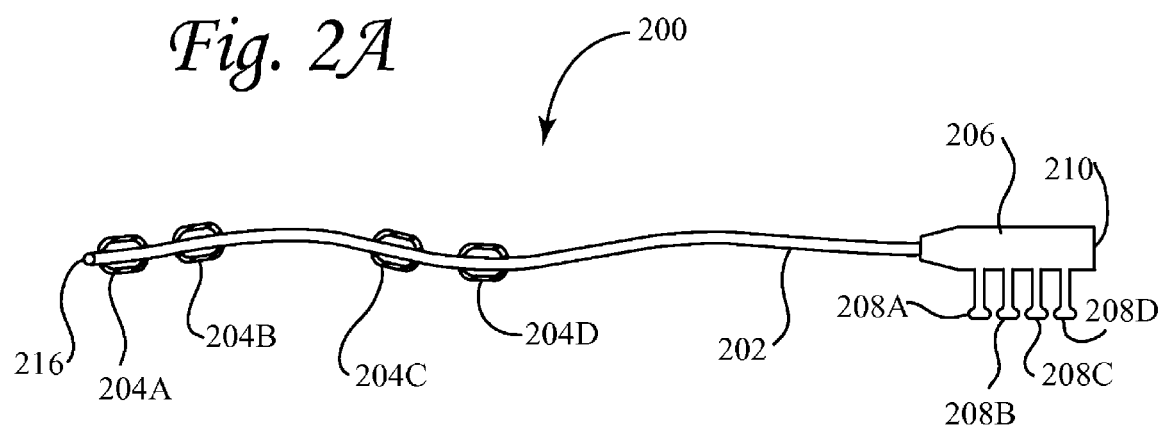
FIG. 2A is a side view of an illustrative embodiment of a catheter device in accordance with the present invention.
Figure 2B:
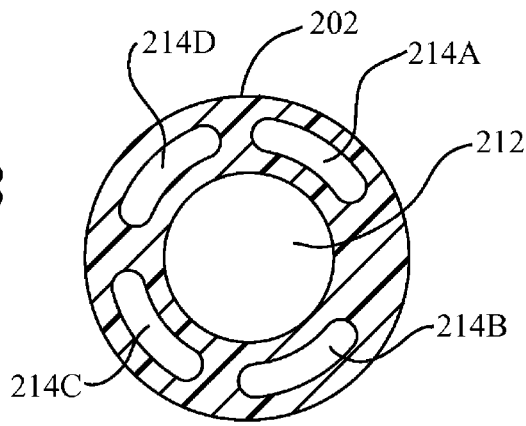
FIG. 2B is a cross-sectional view of the catheter shaft of the catheter device of FIG. 2A.

FIGS. 2A and 2B depict a catheter device 200 in accordance with the present invention. The device 200 includes a hollow elongate flexible catheter shaft 202 with four distally-mounted expandable balloons 204A, 204B, 204C, 204D. The four balloons are spaced apart along the distal portion of the shaft 202.

Figure 2C:
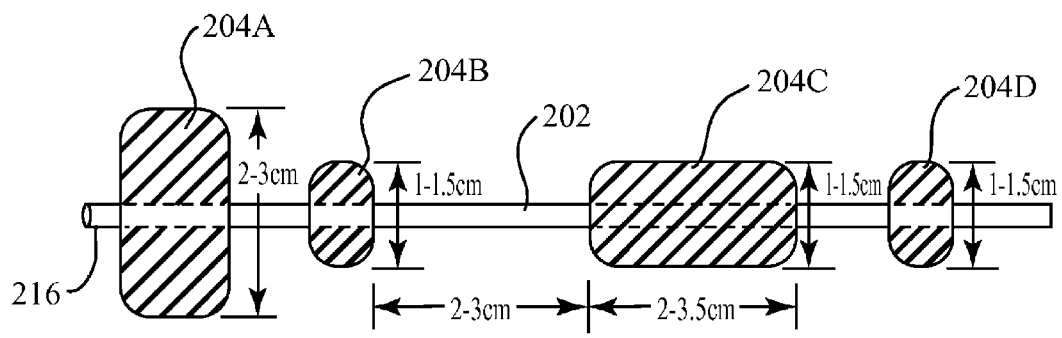
FIG. 2C is a schematic illustration of the size and spacing of the inflatable balloon members of the catheter device of FIGS. 2A and 2B.

The distal-most balloon 204A, which is referred to herein as the "seating balloon," is preferably positioned at or near the distal end of the shaft 202 and is expandable to a maximum radial dimension preferably in the range between 2.5 cm and 3.5 cm (most preferably, the maximum radial dimension is 3.0 cm) as shown in FIG. 2C.

The balloon 204B is proximally located from balloon 204A by a spacing preferably in the range less than 1 cm and is expandable to a maximum radial dimension preferably in the range between 1.0 cm and 1.5 cm as shown in FIG. 2C.

The balloon 204C is proximally located from balloon 204B by a spacing in the range between 2.0 cm and 3.0 cm and is expandable to a maximum radial dimension preferably in the range between 1.0 cm and 1.5 cm as shown in FIG. 2C. In its expanded state, the lengthwise dimension L of balloon 204C along the central axis of the catheter shaft 202 is preferably in the range from 1.0 cm to 3.5 cm. With the lengthwise dimension of balloon 204C in the range between 2.0 cm to 3.5 cm (or longer), the balloon 204D can possibly be omitted from the device. In this manner, balloon 204D is optional and need not be part of all designs.

The optional balloon 204D is proximally located from balloon 204C by a spacing preferably in the range between 1.0 cm and 2.0 cm and is expandable to a maximum radial dimension preferably in the range between 1.0 cm and 1.5 cm as shown in FIG. 2C.

Note that the dimensions and spacing of the balloons 204A, 204B, 204C and 204D correspond to the size and spacing of the iliac arterial and venous systems as will become evident from the operation of the catheter device 200 as set forth below.

The proximal end of the catheter device 200 is provided with a multi-port adapter 206. The adapter 206 has ports 208A, 208B, 208C, 208D and a main access port 210. The first port 208A is in fluid communication with the balloon 204A. The second port 208B is in fluid communication with the balloon 204B. The third port 208C is in fluid communication with the balloon 204C. The fourth port 208D is in fluid communication with the balloon 204D. The main access port 210 is in fluid communication with a distal port 216 on the distal end of the catheter shaft 202. The catheter device 200 can be introduced into the vasculature by an introducer sheath as is well known. The catheter shaft 202 can extend through the introducer sheath and be fixated thereto by mechanical means such as a screw in cap or other suitable shaft fixation mechanism.

As shown in FIG. 2B, the hollow elongate catheter shaft 202 has a main inner lumen 212 and four inflation lumens 214A, 214B, 214C, 214D. The main lumen 212 extends in fluid communication between the main access port 210 and the distal port 216. The first inflation lumen 214A extends in fluid communication between the first port 208A and the balloon 204A. The second inflation lumen 214B extends in fluid communication between the second port 208B and the balloon 204B. The third inflation lumen 214C extends in fluid communication between the third port 208C and the balloon 204C. The fourth inflation lumen 214D extends in fluid communication between the fourth port 208D and the balloon 204D. The four inflation lumens 214A, 214B, 214C, 214D allow for independent inflation and deflation of the four balloons 204A, 204B, 204C, 204D by pumping a fluid (such as a saline solution or air or other medium) into and from the balloons via the ports 208A, 208B, 208C, 208D, respectively.

In the event that the balloon 204D is omitted from the design, the fourth port 208D and corresponding inflation lumen 214D can also be omitted from the design.

The main lumen 212 and the distal port 216 may be used to pass a wide variety of surgical devices (such as guide wires, angioscopes, irrigation lines, vascular grafts and the like) into the vasculature of the patient.

The catheter shaft 202 preferably has an external diameter preferably in the range between 6 and 8 french such that it can be introduced into a femoral artery (or a femoral vein) and advanced from below into the descending aorta (or inferior vena cava). The spacing of the balloons 204A, 204B, 204C and 204D along the distal portion of the catheter shaft 202 allows these balloons to be positioned along the iliac arterial (or venous) vasculature. As described below in detail, the fixation balloon 204A is inflated and located at the bifurcation 14 (or 114), and thus acts to fix the position of the catheter device 200 in the iliac arterial (or venous) vasculature. The other balloons are inflated in order to isolate and occlude blood flow through a portion of the common iliac artery (or vein) traversed by the catheter device 200. This isolated vessel portion can then be used for an anastomosis as part of a kidney transplantation procedure. Such operations will generally require that the length of the catheter shaft 202 be at least 50 cm.

The flexible catheter shaft 202 may be formed of conventional polymers (e.g., polyethelene, polyvinyl chloride, PTFE, PEBAX® and the like. The occluding balloons may be formed of conventional polymer sheet material and the like as is well known in the art. The catheter shaft 202 and/or the occluding balloons 204A, 204B, 204C, 204D may incorporate radio-opaque material to facilitate advancement and placement of the catheter utilizing fluoroscopic imaging techniques.

Figure 3A:
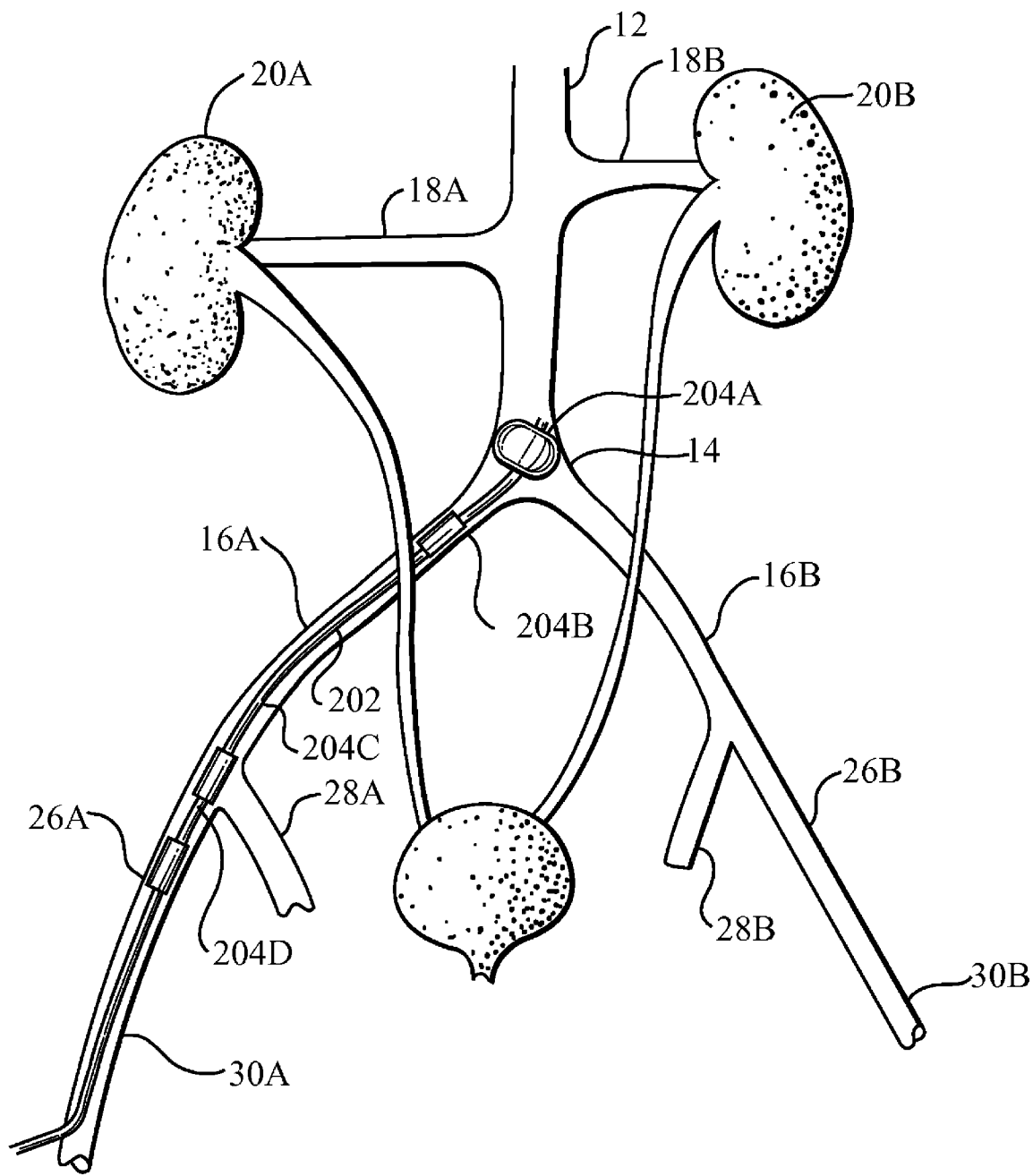
FIGS. 3A-3E are schematic illustrations showing the advancement and placement of the catheter device of FIGS. 2A-2C into the iliac arterial vasculature for selectively isolating and occluding a portion of one branch of the iliac arterial vasculature in accordance with the present invention.
Figure 3B:
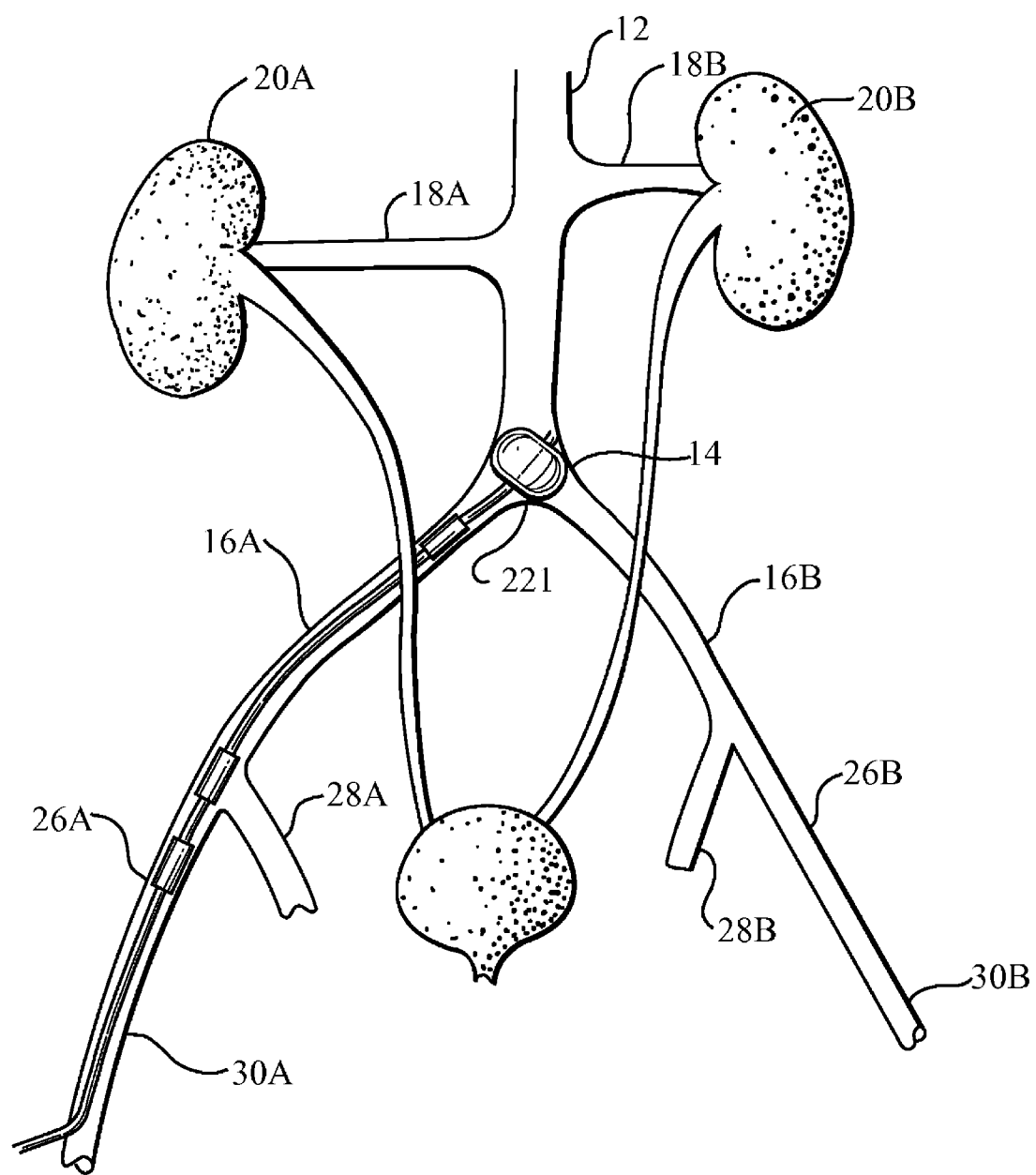

FIG. 3A illustrates the catheter 200 with the inflatable balloons 204A, 204B, 204C, 204D disposed with the iliac arterial vasculature of a patient. The catheter shaft 202 is introduced into the left femoral artery 30A and advanced through the left external iliac artery 26 and common iliac artery 16A past the iliac bifurcation 14 and into the lower end of the abdominal aorta 12 as shown. The seating balloon 204A is inflated (as shown) and then the catheter shaft 202 is retracted proximally such that the seating balloon 204A is positioned at the iliac bifurcation 14 as shown in FIG. 3B. In this manner, the seating balloon 204A, when inflated, fixes the distal portion of the catheter device 200 in the iliac arterial vasculature as shown. The seating balloon 204A can also function to occlude or restrict blood flow from common iliac artery 16A into the iliac bifurcation 14. Preferably, the seating balloon 204 does not occlude blood flow from the other common iliac artery 16B. For example, it can be sized such that space remains between the vessel wall of the iliac bifurcation 14 and the balloon 204A to allow blow flow around the balloon. Alternatively, the balloon 204A can provide a flow path through the balloon (depicted by dotted lines 221) that allows for blood flow from the common iliac artery 16B to the iliac bifurcation 14.

Figure 3C:
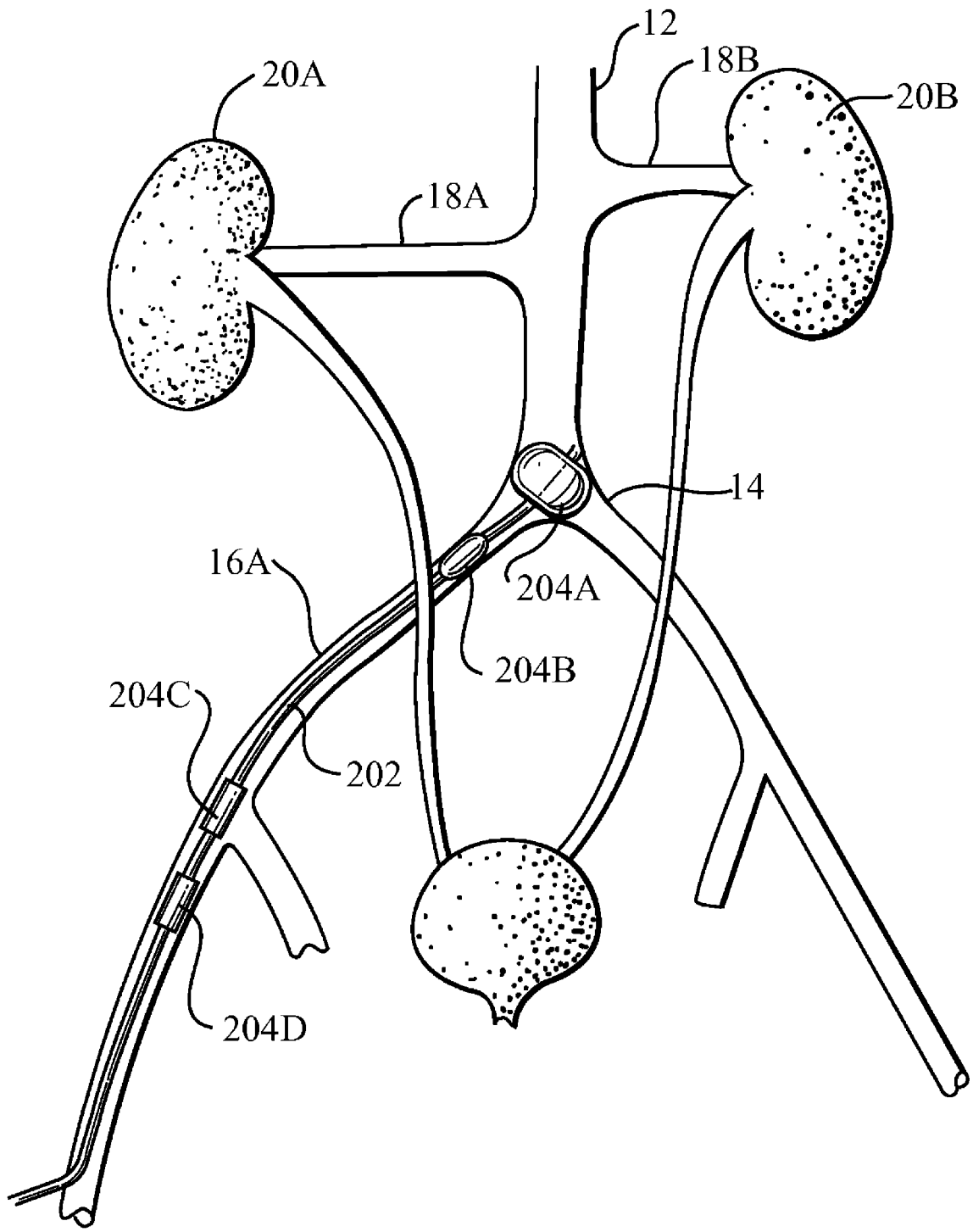

With the catheter device 200 fixed in position (e.g., with the balloon 204A located at the iliac bifurcation 14), the balloon 204B is inflated as shown in FIG. 3C. The balloon 204B is positioned and sized such in its inflated state it sealably contacts the interior vessel wall of the common iliac artery 16A and occludes blood flow from upstream of the balloon 204B toward the seating balloon 204A at the iliac bifurcation 14. The contact of the inflated balloon 204B to the interior vessel wall of the common iliac artery 16 also acts to fixate and hold the position of the catheter device 200 in the iliac arterial vasculature of the patient.

Figure 3D:
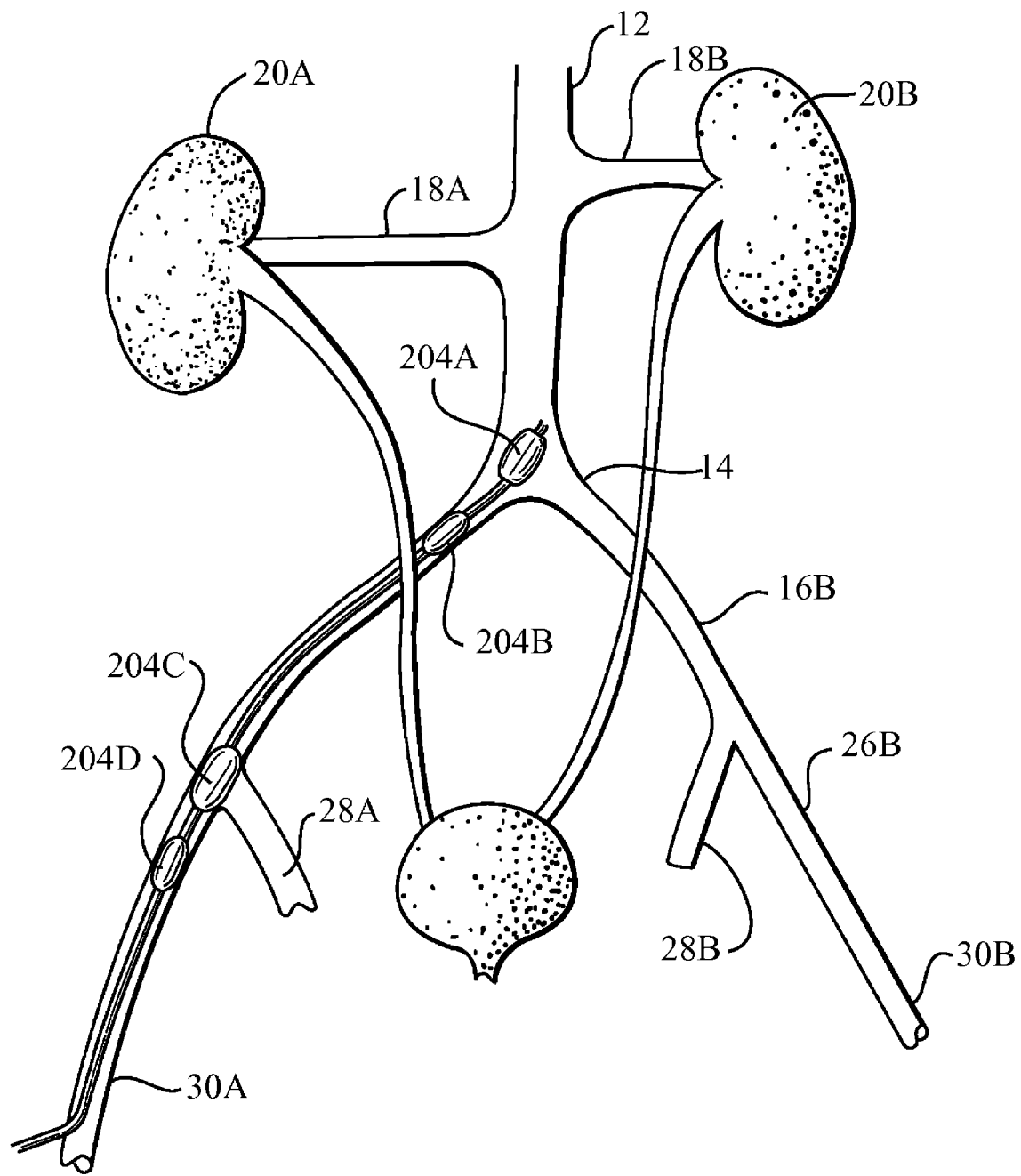

After the balloon 204B is inflated, the balloon 204C and possibly the balloon 204D are inflated as shown in FIG. 3D. The balloon 204C is positioned and sized such in its inflated state it sealably contacts the interior vessel wall at or near the bifurcation point of the common iliac artery 16A to the left external iliac artery 26A and the left internal iliac artery 26B and occludes blood flow from upstream of the balloon 204C toward the balloon 204B. In the preferred embodiment, the lengthwise dimension of balloon 204C in its expanded state is in the range between 2.0 cm to 3.5 cm (or longer), which is designed to traverse the entire length of the bifurcation point of the common iliac artery 16A to the left external iliac artery 26A and the left internal iliac artery 26B as shown in FIG. 3D. In this configuration, it may be possible to omit the balloon 204D. When used, the balloon 204D is positioned and sized such in its inflated state it sealably contacts the interior vessel wall of the left external iliac artery 26A and occludes blood flow from upstream of the balloon 204D toward the balloon 204C. With the balloon 204B in its inflated state and fixing the position of the catheter, the balloon 204A can be deflated as shown in FIG. 3D to provide for increased blood flow from the common iliac artery 16B to the iliac bifurcation 14.

Figure 3E:
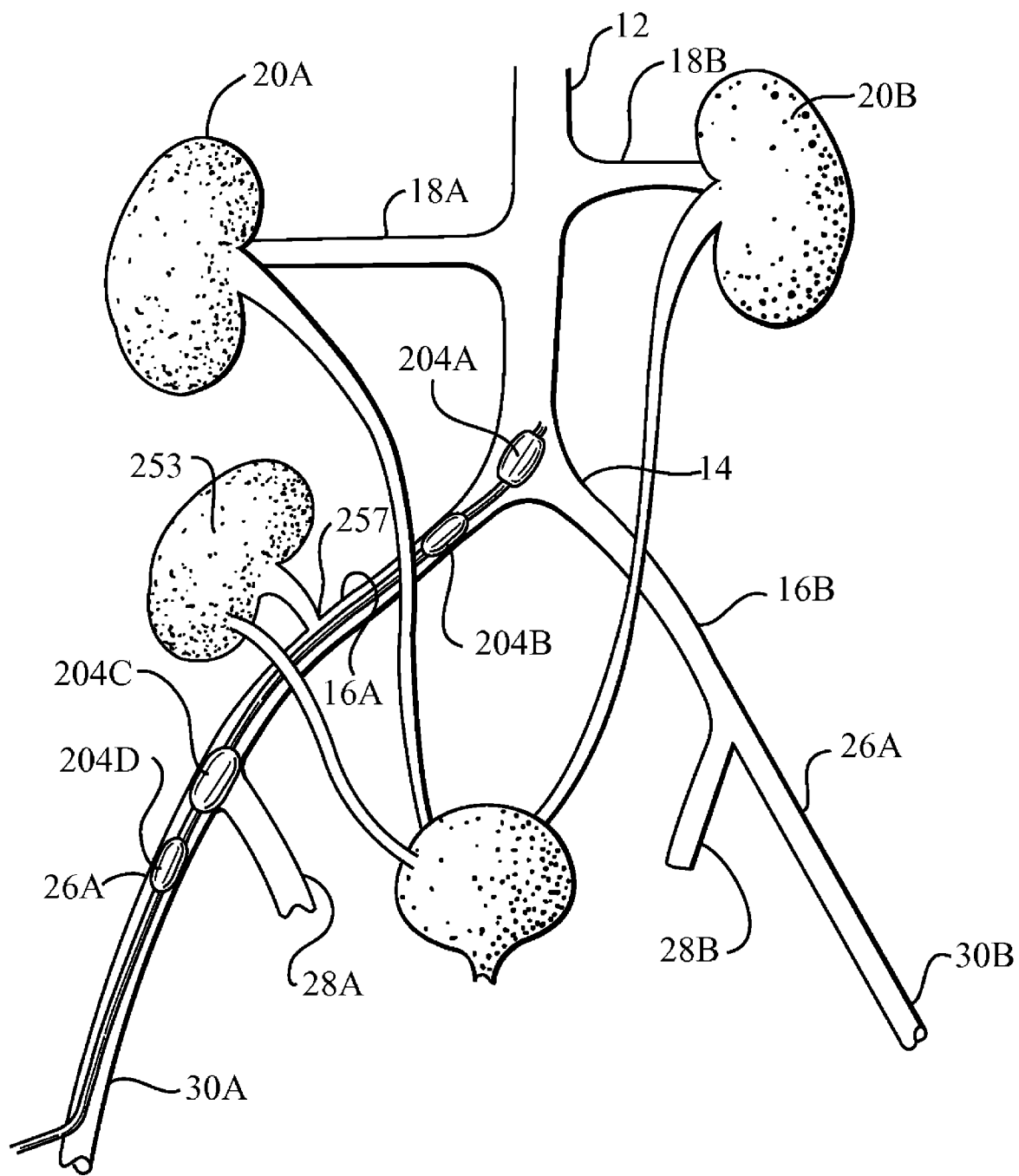

In their inflated states, the balloons 204B and 204C isolate and occlude blood flow through the portion of the common iliac artery 16A therebetween. This isolated vessel portion can then be used for an anastomosis 231 to a donor kidney 253 as part of a kidney transplantation procedure as shown in FIG. 3E. In their inflated states, the balloons 204C and 204D isolate and occlude blood flow through the portion of the left external iliac artery 26A therebetween. This isolated vessel portion can also be used for an anastomosis to a donor kidney as part of a kidney transplantation procedure similar to that shown in FIG. 3E. After the anastomosis is complete, the balloons can be deflated and the catheter device 200 retracted and removed from the iliac vasculature.

Advantageously, the catheter device of the present invention can be quickly fixated within the iliac vasculature and manipulated in order to efficiently isolate and occlude a portion of the iliac vasculature (preferably a portion of the common iliac artery or common iliac vein). The fixation of the catheter device within the iliac vasculature can be accomplished without the need for fluoroscopic imaging techniques. The isolation and occlusion of the iliac vasculature provided by the catheter device is suitable for preparing the isolated iliac vascular portion for an anastomosis as part of a kidney transplantation procedure. Such isolation and occlusion is performed in a minimally invasive manner that reduces the risk of bleeding at the occlusion sites (as compared to clamping). It also reduces the risk of dislodging plaque at the occlusion sites (as compared to clamping), and thus reduces the risk of a plaque-induced embolism being carried to the foot or brain, which can cause gangrene in the foot or a stroke in the brain.

The catheter device of the present invention can also be used to repair an aortic or abdominal aneurysm. In many cases, such repair involves introduction of a stent through a femoral artery. In some cases, the size of the femoral artery is smaller than the shaft of the stent. In these cases, the surgeon must isolate and clamp an iliac artery in order to a construct a conduit for the stent that is larger than the stent shaft size. The isolation and clamping of the iliac artery requires significant dissection and carries a risk of damaging the neighboring tissues. Also one needs a longer incision to isolate the iliac arteries. The catheter device of the present invention can be used to isolate and occlude a portion of the iliac artery. After such isolation and occlusion, the surgeon can make an incision preferably on the top part of the isolated iliac artery portion. The stent can then be introduced by a conduit through this incision.

There have been described and illustrated herein several embodiments of a catheter device with multiple expandable elements and a method of operating the catheter for efficiently isolating and occluding a portion of the iliac vasculature. While particular embodiments of the invention have been described, it is not intended that the invention be limited thereto, as it is intended that the invention be as broad in scope as the art will allow and that the specification be read likewise. Thus, while particular examples described herein relate to the left branch of the iliac vasculature, the catheter as described herein can be used to isolate and occlude a portion of the right branch of the iliac vasculature and/or the left or right branches of the iliac venous system. Moreover, while particular occluding balloons have been disclosed, it will be appreciated that other occluding elements, such as conical shaped expanding elements or cylindrical-shaped expanding elements, can be used as well. Moreover, the expandable size of such elements can also be controlled by mechanical means such as wires or the like. In addition, while a particular configuration of the multi-lumen catheter shaft has been disclosed, it will be appreciated that other multi-lumen configurations, such as a sequence of concentric lumens formed about the inner guide lumen, can be used. Also, while particular configurations and sizes have been disclosed in reference to elements of the catheter, it will be understood that the aortic catheter described herein can be readily adapted to other configurations and sizes. For example, the device can readily be adapted to include more than four (or less than four) occluding elements and supporting inflation lumens/ports. Also, the outside diameter of the device can readily be adapted to different sizes and distances such that the device is suitable for different size patients, such as a smaller diameter catheter for pediatric patients. Similarly, the distance between balloons can readily be adapted. It will therefore be appreciated by those skilled in the art that yet other modifications could be made to the provided invention without deviating from its spirit and scope as claimed.

What is claimed is:

1. A surgical method for isolating and occluding a portion of the iliac vasculature of a patient which branches from an iliac bifurcation of the patient, comprising:
with a catheter for accessing the iliac vasculature, the catheter including an elongate catheter shaft and a plurality of independently expandable members, the catheter shaft advanceable though the iliac vasculature and having a proximal portion that extends out from the patient and a distal portion adapted to be disposed within the iliac vasculature, and the plurality of independently expandable members disposed on said distal portion of said catheter shaft, wherein said expandable members includes a first expandable member dimensioned and configured so that it rests within the iliac bifurcation leading to the common iliac arteries or veins when expanded so as to fixate the catheter within the iliac vasculature, and wherein at least two other expandable members are spaced apart proximally from said first expandable member and configured to selectively isolate and occlude blood flow through the portion of the iliac vasculature when expanded,
a) advancing the catheter shaft in a distal direction through the iliac vasculature towards the iliac bifurcation such that said first expandable member is disposed distally beyond the common iliac arteries or veins;
b) expanding said first expandable member and moving said catheter shaft in a proximal direction opposite said distal direction with the first expandable member expanded such that said first expandable member is seated within the iliac bifurcation and said other expandable members are disposed in the iliac vasculature proximal to said first expandable member seated within the iliac bifurcation; and
c) expanding at least one of the other expandable members to selectively isolate and occlude blood flow through the portion of the iliac vasculature proximal to said first expandable member.

2. A method according to claim 1, wherein:
said expandable members are inflatable balloons whose inflation levels are independently controlled by fluidic pressure supplied to said balloons via inflation lumens integral to said catheter shaft, and wherein the expanding steps iii) and iv) are accomplished by adjusting fluidic pressure to the respective inflatable balloon to increase the inflation level of the respective balloon.

3. A method according to claim 1, wherein:
said other expandable members includes a second expandable member disposed in the iliac vasculature adjacent the bifurcation point of the common iliac artery or vein to the external iliac artery or vein and the internal iliac artery or vein.

4. A method according to claim 1, further comprising:
prior to said advancing the catheter shaft, introducing said catheter shaft into the femoral artery or vein of the patient.

5. A method according to claim 1, wherein:
the catheter shaft is fixated within the iliac vasculature of the patient without fluoroscopic imaging.

6. A method according to claim 1, further comprising:
performing an anastomosis to a donor kidney at the portion of the iliac vasculature.

7. A method according to claim 1, further comprising:
making an incision into the portion of the iliac vasculature for introducing a stent through a conduit therethrough.

8. A method according to claim 3, wherein:
said other expandable members includes a third expandable member disposed in the iliac vasculature between said first expandable member and said second expandable member.

9. A method according to claim 8, wherein:
said other expandable members includes a fourth expandable member disposed in the iliac vasculature proximal to the second expandable member.

10. A method according to claim 1, wherein:
said advancing the catheter shaft in a distal direction comprises advancing the catheter shaft such that said first expandable member is disposed in a descending aorta of the patient.

11. A method according to claim 1, wherein:
said advancing the catheter shaft in a distal direction comprises advancing the catheter shaft such that said first expandable member is disposed in an inferior vena cava of the patient.

* * * * *